(12) United States Patent
Fang et al.

(10) Patent No.: US 6,877,385 B2
(45) Date of Patent: Apr. 12, 2005

(54) CONTACT TYPE MICRO PIEZORESISTIVE SHEAR-STRESS SENSOR

(75) Inventors: Yean-Kuen Fang, Tainan (TW); Ming-Shanng Ju, Tainan (TW); Jyh-Jier Ho, Tainan (TW); Gin-Shin Chen, Chang-hug (TW); Ming-Chun Hsieh, Tainan (TW); Shyh-Fann Ting, Kaohsiung (TW); Chung-Hsien Yang, Tainan (TW)

(73) Assignee: National Science Council, Taipei (TW)

( * ) Notice: Subject to any disclaimer, the term of this patent is extended or adjusted under 35 U.S.C. 154(b) by 449 days.

(21) Appl. No.: 10/085,256

(22) Filed: Oct. 22, 2001

(65) Prior Publication Data

US 2002/0174727 A1 Nov. 28, 2002

(30) Foreign Application Priority Data

Nov. 16, 2000 (TW) ........................................ 89124498 A

(51) Int. Cl.⁷ ................................................ G01B 7/16
(52) U.S. Cl. ............................................ 73/777; 73/841
(58) Field of Search .......................... 73/760, 777, 774, 73/781, 841

(56) References Cited

U.S. PATENT DOCUMENTS

| | | | | |
|---|---|---|---|---|
| 4,333,349 A | * | 6/1982 | Mallon et al. | ................. 73/708 |
| 4,442,717 A | | 4/1984 | Kurtz et al. | .................... 73/766 |
| 4,456,901 A | * | 6/1984 | Kurtz et al. | .................... 338/4 |
| 4,680,606 A | * | 7/1987 | Knutti et al. | ................ 257/419 |
| 5,408,112 A | * | 4/1995 | Tai et al. | ...................... 257/254 |
| 5,522,266 A | * | 6/1996 | Nicholson et al. | ............. 73/708 |
| 6,040,900 A | | 3/2000 | Chen | ......................... 356/35.5 |
| 6,044,705 A | | 4/2000 | Neukermans et al. | ..... 73/504.02 |

OTHER PUBLICATIONS

M. Zhang, et al, "Frictional Action at Lower Limb/Prosthetic Socket Interface", Med. Eng. Phy. vol. 18, No. 3, pp 207–214, 1996.

M. Zhang, Arthur F.T. Mak, "A Finite Element Analysis of the Load, etc.", IEEE Transactions on Rehab, Eng., vol.4, No.4,pp337–346, 1996.

Jyh–Jier Ho, et al, "Development of a Micro–Electro–Mechanical System Pressure Sensor for Rehabilitation Engineering Applications", International J. of Electronics, vol. 87. No. 6, pp757–767.(2000).

Chang Liu, et al, "A Micromachined Flow Shear–Stress Sensor Based on Thermal Transfer Principles", J. of MEMS, vol.8,No. 1,pp90–99, 1999.

Tao Pan, et al/ "Microfabricated Shear–Stress Sensors, Part 1: Design and Fabrication", AIAA J., vol.37, No. 1, pp66–72, 1999.

Jávad Shajii, et al, "A Micromachined Floating Element Shear Stress Sensor Using Wafer–Bonding Technoloty", J. of MEMS,vol.1,No.2,pp89–94,1992.

A. Padmanabhan, et. al. "Micromachined sensors for static and dynamic shear–stress measurement in aerodynamic flows," Transducers' 97, pp. 137–140. 1997.

* cited by examiner

*Primary Examiner*—Max Noori
(74) *Attorney, Agent, or Firm*—Bucknam & Archer

(57) ABSTRACT

There is disclosed a semiconductor sensor for measuring the contact shear stress distribution between the socket of an above-knee (AK) prostheses and the soft tissue of an amputee's stump. The sensor is fabricated by the micro-electro-mechanical system (MEMS) technology, and its main sensing part is 2-X shaped with a flange structure. The sensor is prepared by anisotropic wet etching of bulk silicon in KOH solution and a square flange above the sensing diaphragm is formed through surface micromachining of deposited $SiO_2$ thin film. This invention has the following characteristics: piezo-resistivity of the monolithic silicon will be utilized to convert shear deformation of the sensor into an electrical signal and a micro sensor which can measure the shear force vector acting on the sensing flange.

5 Claims, 21 Drawing Sheets

(2 of 21 Drawing Sheet(s) Filed in Color)

CONTACT TYPE MICRO PIEZORESISTIVE SHEAR-STRESS SENSOR

FIELD OF THE INVENTION

This article is to present an invention that utilizes the micro-electro-mechanical (MEMS) technology to produce Contact-type piezoresistive Shear-Stress sensors which can be applied in the Above-knee Prosthesis rehabilitation engineering. The primary sensing units of these kinds of Shear-Stress sensors are the X-shape piezoresistors at the four ends, each with a flange on it. Such a structure is determined according to the results of finite element method (FEM) analysis.

BACKGROUND OF THE INVENTION

As accidents happen frequently, the number of amputees is considerably increasing these days. Inaptitude to move, due to injuries, often turns out to be both a pain to the patient himself and a burden to his family and the society. The only way to relieve this bad condition is rehabilitation. On the rehabilitation engineering for the amputated, Above-knee Prosthesis has been playing an important role. In general, this kind of Above-knee Prosthesis, reported by M. S. Ju et al. on *JSME International Journal*. (Vol.38, No.1, pp.78–86, 1995), can be divided into five main parts: socket, artificial knee joint, movement controlling unit, shank sheath, and prosthesis. Having lost their knee joints, the above-knee amputees are driven by innominate muscles to walk. The driving force is transmitted via an artificial knee joint to the stump. However, whether amputees agree to use prostheses depends mostly on the contact conditions between a stump and the socket mounted on it.

An adequate prosthesis socket should take into account the shape and sewing-up condition of a stump. For the amputees that wear prostheses, skin of the stumps may be hurt, and even worse, the subcutaneous blood circulation may be oppressed, by Normal Pressure and Shear-Stress stresses distributed on the interface owing to a close contact between the stumps and sockets. Thus, acceptability of prostheses and adaptability of amputees are badly influenced. So, if the distributions and sizes of the stresses can be measured and analyzed, and then presented for the reference of the prosthesis masters to amend the socket shapes, comfort of the prosthesis wearers will surely be improved greatly. According to the reports of M. Zhang et al. on *Medical Eng. Phy., (Vol.* 18, No.3, pp.207–214, 1996) a 3-D FEM model had been used to study the friction coefficient between below-knee sockets and stump skin and to measure the stresses between the contacting faces through experiments. They found that the Shear-Stress stress increased with the friction coefficient, and was more likely to hurt stump skin. As to the above-knee prostheses, M. Zhang et al. reported on *IEEE Trans. on Rehabilitation Eng.*, (Vol. 4, No.4, pp. 337–346, 1996) that only a 2-D FEM model was made to study the friction coefficient between the contacting surfaces. They also inferred that the penetrating pain of prosthesis wearers decreased with the value of the friction coefficient, and thus suggested a reasonable coefficient should be maintained to keep a small Shear-Stress and prevent prostheses from slipping. However, no experiments were carried out to verify this inference. On clinic, most of the sockets are made according to experience. To improve the wearing comfort and enhance the design level of prostheses, therefore, it is necessary to develop a proper sensor to measure the stress and strain caused by Normal Pressure and Shear-Stress between sockets and stumps while prosthesis wearers are walking.

At present, the fluid-field micro Shear-Stress sensors are divided into two types: direct and indirect measuring. Differences between these two types: thermal Shear-Stress sensors have a simpler but stronger structure, and can be produced easily; however, it is difficult to do calibration for this type, and heating and fluid problems should also be considered carefully. It is hardly possible to equip such a system between the socket and the stump skin. The other one is the Floating element Shear-Stress sensor that has a feature of accurate dynamic calibration; however, its defects include uneasy measurement of Shear-Stress and weaker structure while using Floating element. Like the first type, it cannot be applied on the prosthesis sockets just because of no fluids existing.

As to the above-knee amputees, Shear-Stress, as well as Normal Pressure, may cause bitter or even penetrating pains on certain parts. Till now, there is no Shear-Stress sensor applied in domestic Above-knee Prosthesis researches. They are usually used to measure Shear-Stress in the fluid field by home and abroad researchers, who have paid great attention to their high sensitivity despite of their measuring range of only a few Pa's. Apparently, they are not suitable for measuring Shear-Stress between the socket and stump skin. Besides, according to the statement reported by M. Zhang et al. on *IEEE Trans. on Rehabilitation Eng* (Vol. 4, No. 4, pp.337–346, 1996) the maximum Normal Pressure 320K (Pa) appeared between the stump skin and the socket on it while the prosthesis wearer is standing. Therefore, while designing Shear-Stress sensors, allowable errors should be taken into consideration as a force of Normal Pressure 320K (Pa) is applied on the sensing diaphragm; i.e. expecting that almost all the signals produced by the Shear-Stress can be measured by the X-shape piezoresistors. For obtaining more accurate data, Contact-type micro-piezoresistive Shear-Stress sensors is needed which is able to endure 320 K (Pa) Normal Pressure and to measure the Shear-Stress produced between the stump skin and the socket on it. This kind of sensors should also be arranged in arrays on the surface of the stump in order to measure its Shear-Stress, distribution of pressure and other stresses, and their changes in dynamic conditions.

Meanwhile, a practical application of Above-knee Prosthesis is that: except Normal Pressure, Shear-Stress is another important factor that will affect the acceptability of prostheses and the adaptability of prosthesis wearers since the stump skin contacts so closely with the socket of a prosthesis. As the friction coefficient between the stump skin and the socket is increasing, the Shear-Stress will grow more and more, and thus the possibility to hurt the stump skin becomes greater, Therefore, a suitable friction coefficient is needed to avoid slipping of the prostheses and, at the same time, reduce the pain the prosthesis wearers may suffer. So, on the Above-knee Prosthesis rehabilitation engineering, Shear-Stress sensors, not just for vertical pressures, are urgently needed for measuring the distribution and sizes of the stresses caused by the pressures and stressed produced between the stump skin and the socket for the reference of the prosthesis masters to amend the shapes of sockets.

DESCRIPTION OF THE PRIOR ART

An outstanding achievements directed by Jyh-Jier Ho et al. on research of Above-knee Prosthesis sensors for vertical pressures has been reported on International J. of Electronics (vol. 87, No. 6, pp. 757–767, 2000), but as to the study of Shear-Stress sensors, most of the abroad scholars are applying them in measuring Shear-Stress in the fluid field, emphasizing their high sensitivity despite of their measuring range of only a few Pa. Seeing this, it is apparent that this kind of sensors are not suitable for measuring the Shear-Stress between the stump skin and the socket on it.

Generally the fluid-field micro Shear-Stress sensors can be divided into two types: direct and indirect measuring. As for the indirect type, the most representative one is the micro thermal Shear-Stress sensor indicated on MEMS by Chang Liu et al. on *J. of MEMS* (vol. 8, No.1, pp.90–99, 1999). The working principle is: once a fluid flows the sensor that has equipped with a slim heating unit made by deposited Poly Silicon part of the heat on the heating unit will be carried away and thus measured by the sensor. The Shear-Stress value can thus be obtained from the heat measured. For direct measuring, the sensors can be further divided into four types according to signals' sensing methods: capacitor type reported by Tao Pan et al on *AIAA Journal* (vol.37, No.1, pp.66–72, 1999); piezo-electrical type by A. P. Neukerman et al on U.S. Pat. No. 6,044,705 (2000); piezoresistive type by A. D. Kurtz et al. on U.S. Pat. No. 4,442,717 (1984) or by Javad Shajii et al on *J. of MEMS* (Vol. 1, No.2, pp.89–94, 1992); and optical type by X. Chen et al on U.S. Pat. No. 6,040,900 (2000) or by A. Padmanabhan et al on *Transducers'* 97(pp.137–140, 1997). All these four types have a similar structure—when Floating element, used as a fluid, flows through these kinds of sensors, it will shift aside, forced by Shear-Stress. Electronic signals, linear to the Shear-Stress in the fluid field, are received by different sensing methods, such as the optical type, etc. As the Floating element is shifting aside, a diode under the gate will receive different amount of projected rays, and thus produces different current volumes that are linear to the Shear-Stress values.

A comparison of the two types of Shear-Stress sensors: thermal Shear-Stress sensors have simpler and stronger structures and are easily made, but very difficult while in calibration. Besides, heating and fluid problems should also be regarded. So, it is very difficult to mount such systems between the stump skin and the socket. On contrary, the Floating element Shear-Stress sensors offer accurate dynamic calibrating features but are less strong and more difficult in measuring. Similar to the first-mentioned type, this kind of sensors is not suitable for the sockets of the prostheses in which no fluid flows through.

SUMMARY OF THE INVENTION

The primary purpose of the invention is to disclose the contact type micro piezoresistive shear-stress sensor for measuring the shear stress distribution between socket of above-knee (AK) prostheses and the soft tissue of amputee's stump.

The second purpose of the invention is to disclose the preparation processes, therein make anisotropic wet etching of bulk silicon in KOH solution and a square flange.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will now be described by way of example with reference to the accompanying Tables and Figures in which.

The distribution from red to blue stands for the effective stress from maximum to minimum.

Figure 2A:
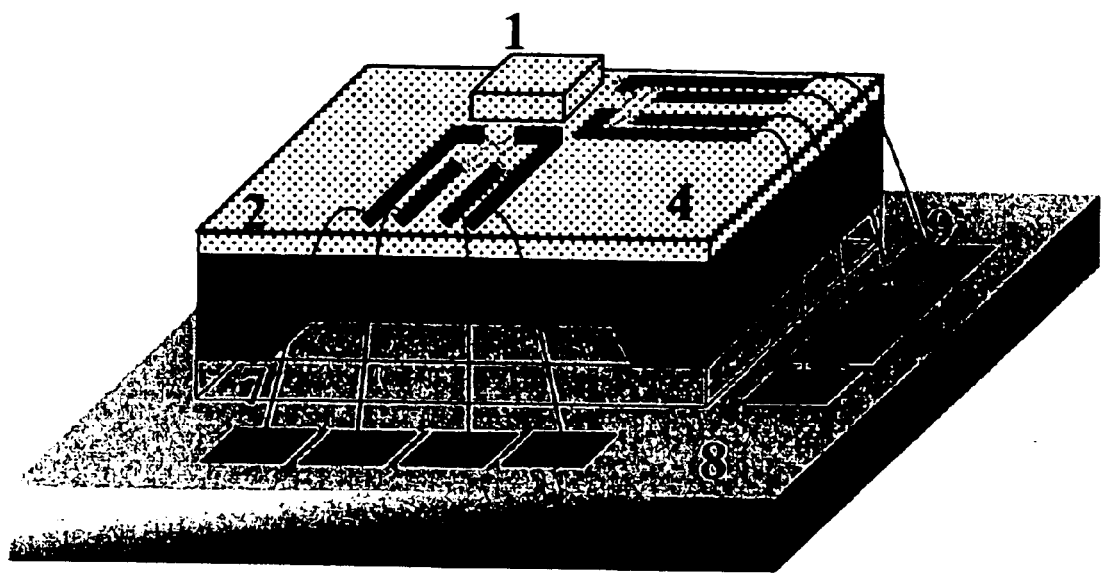
Figure 2B:
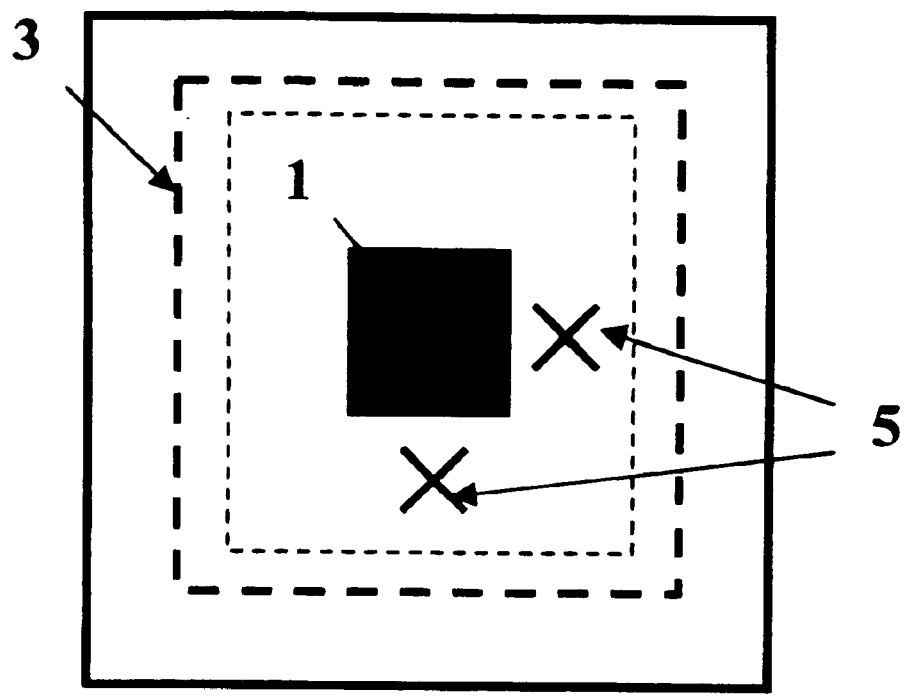
Figure 2C:
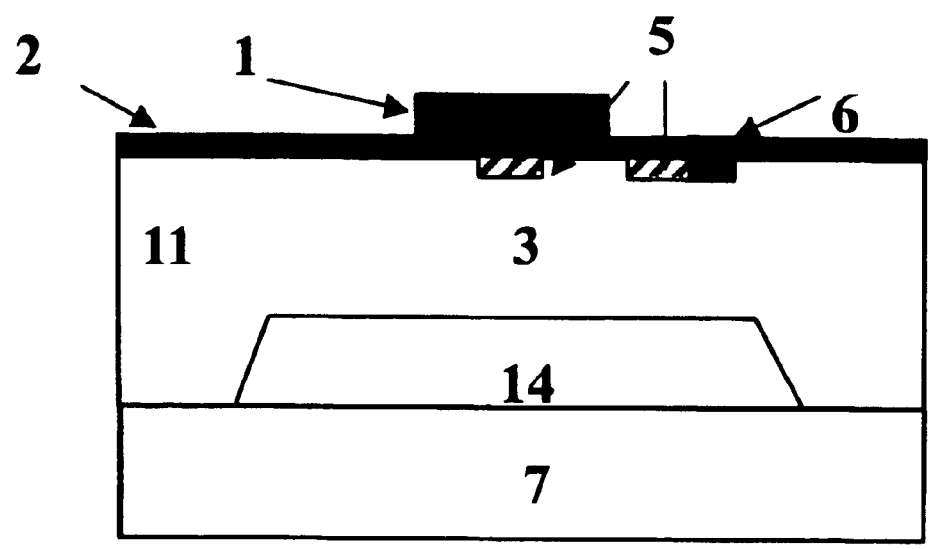
Figure 3A:
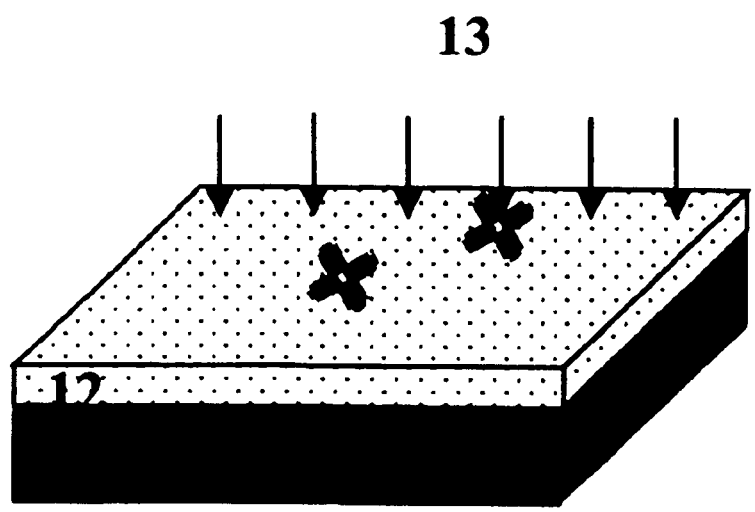
Figure 3B:
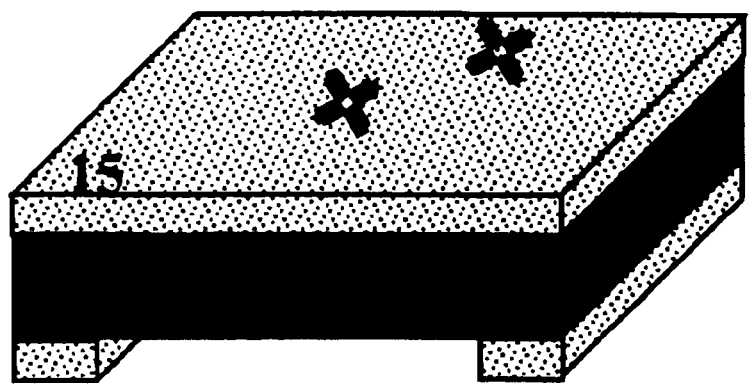
Figure 3C:
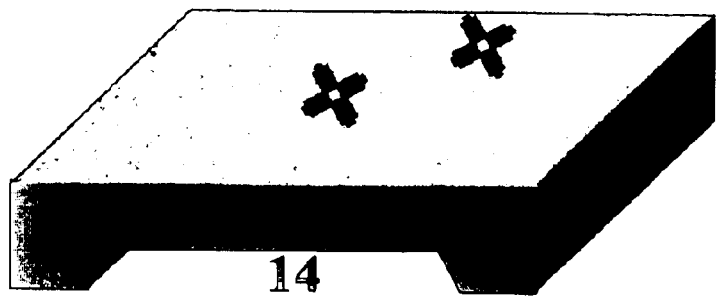
Figure 3D:
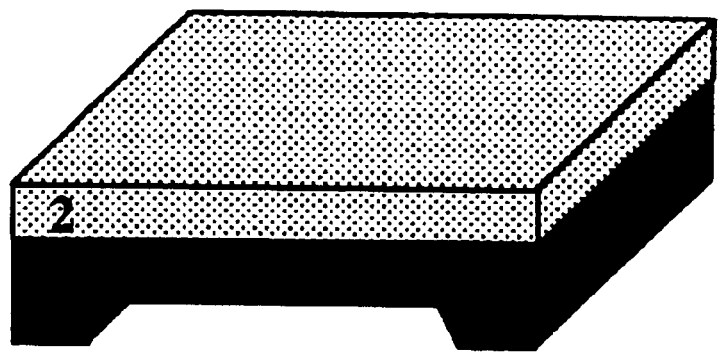
Figure 3E:
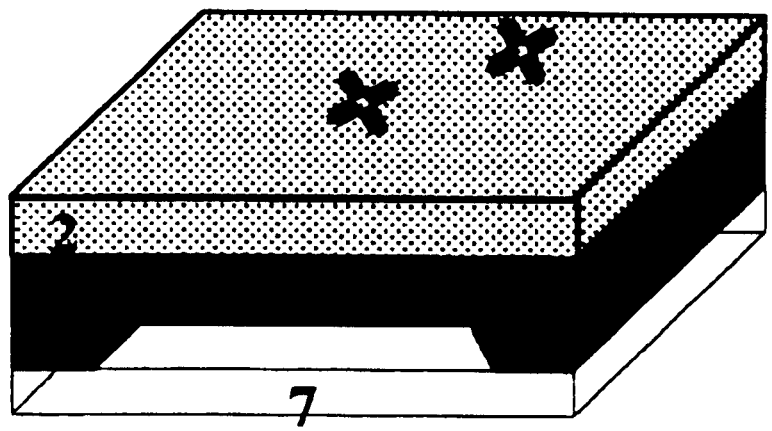
Figure 3F:
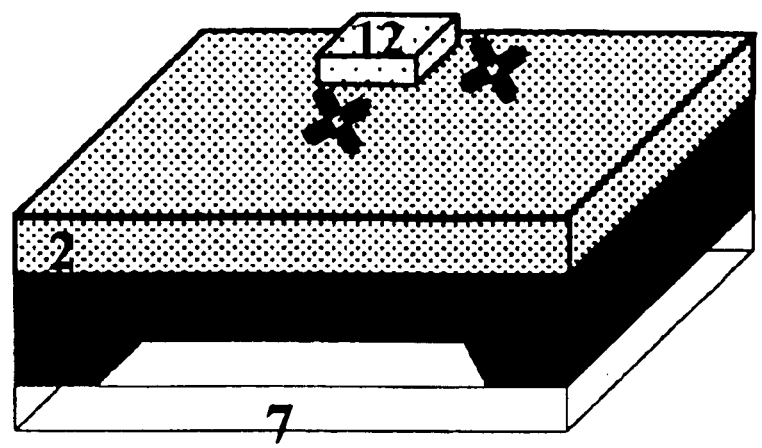
Figure 3G:
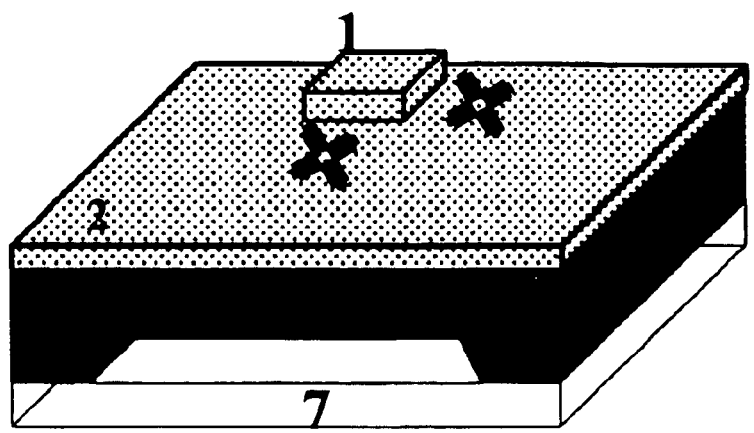
Figure 3H:
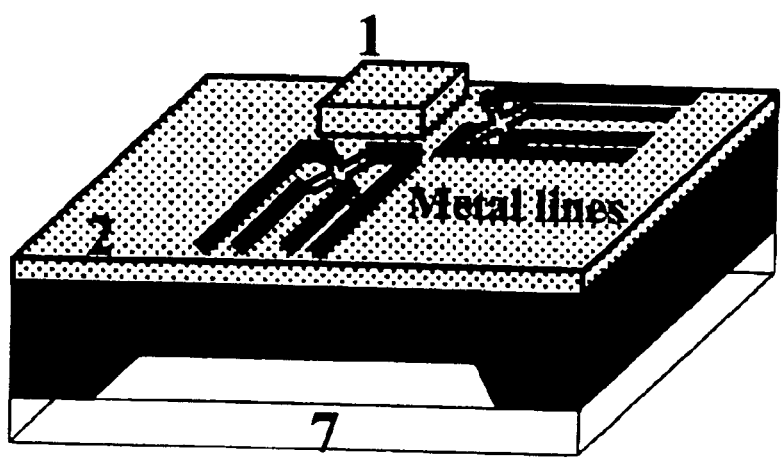
Figure 4:
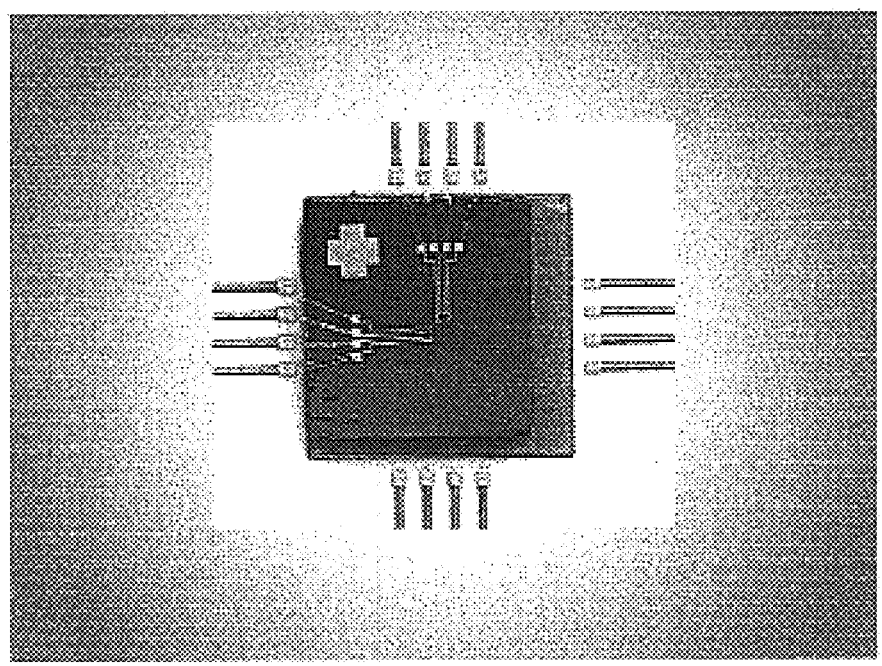
Figure 4:
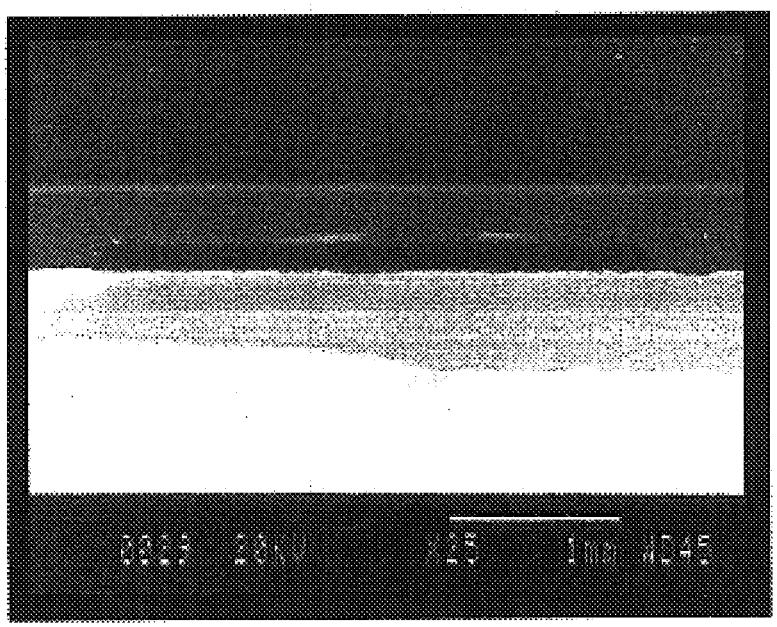
Figure 4:
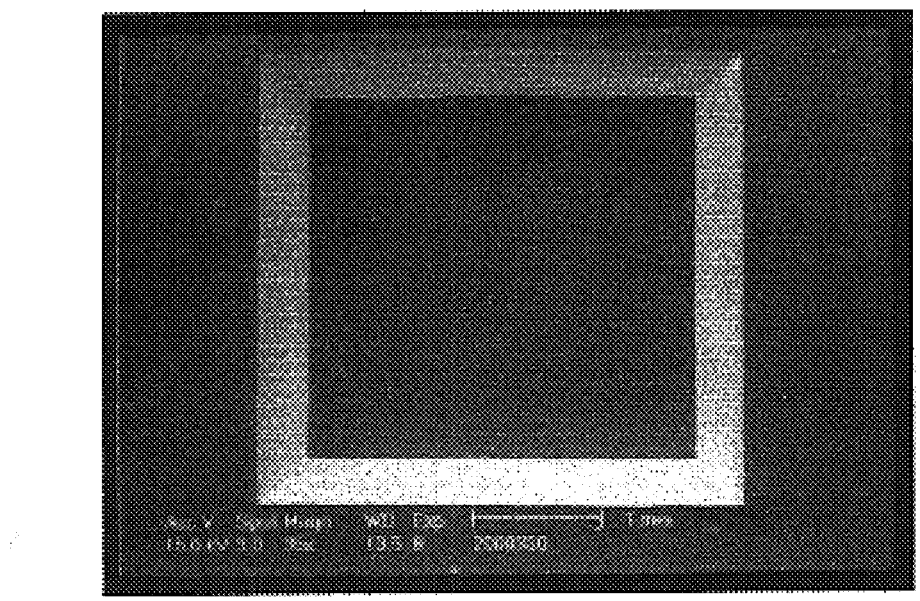
Figure 5:
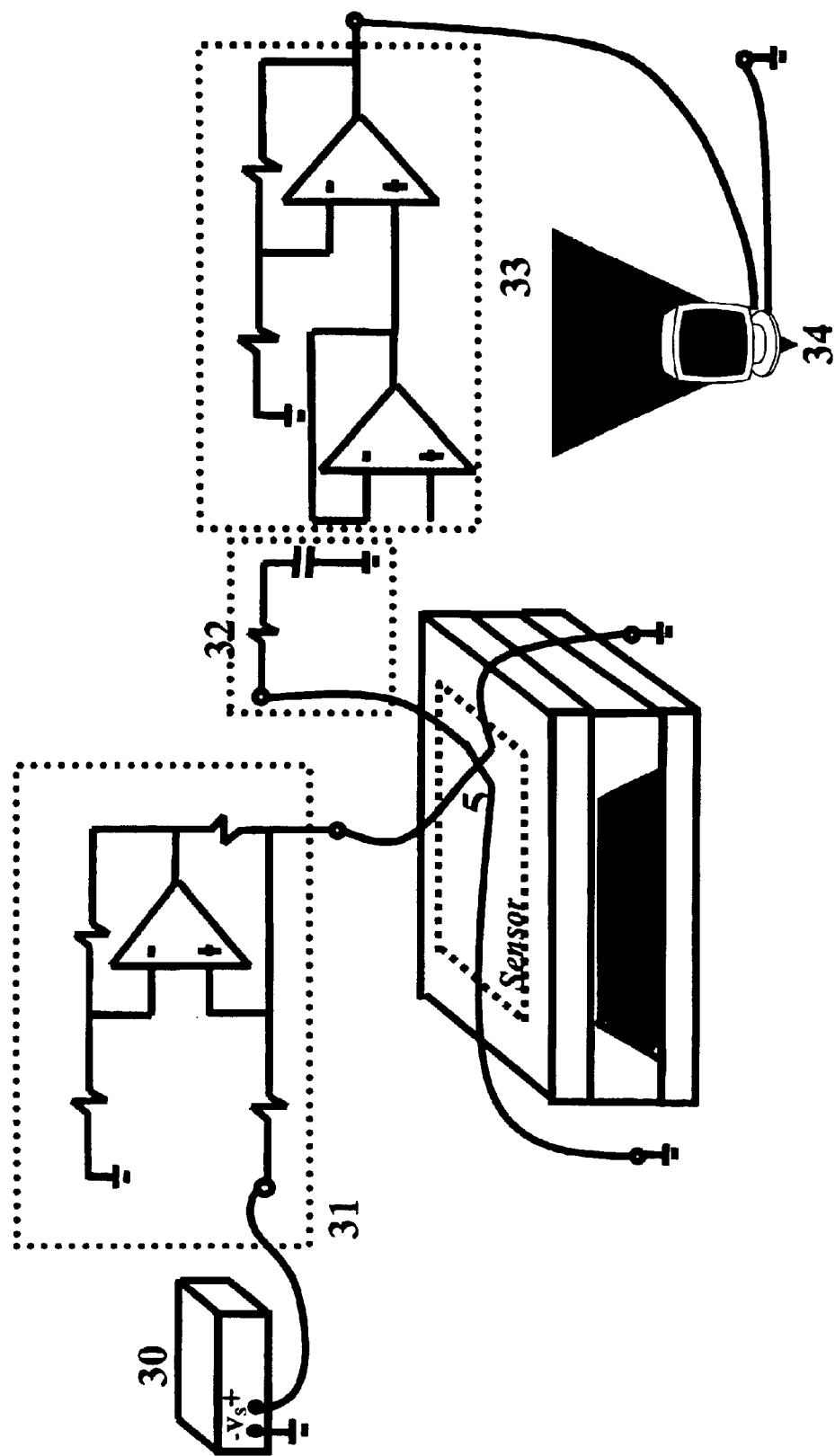
Figure 6:
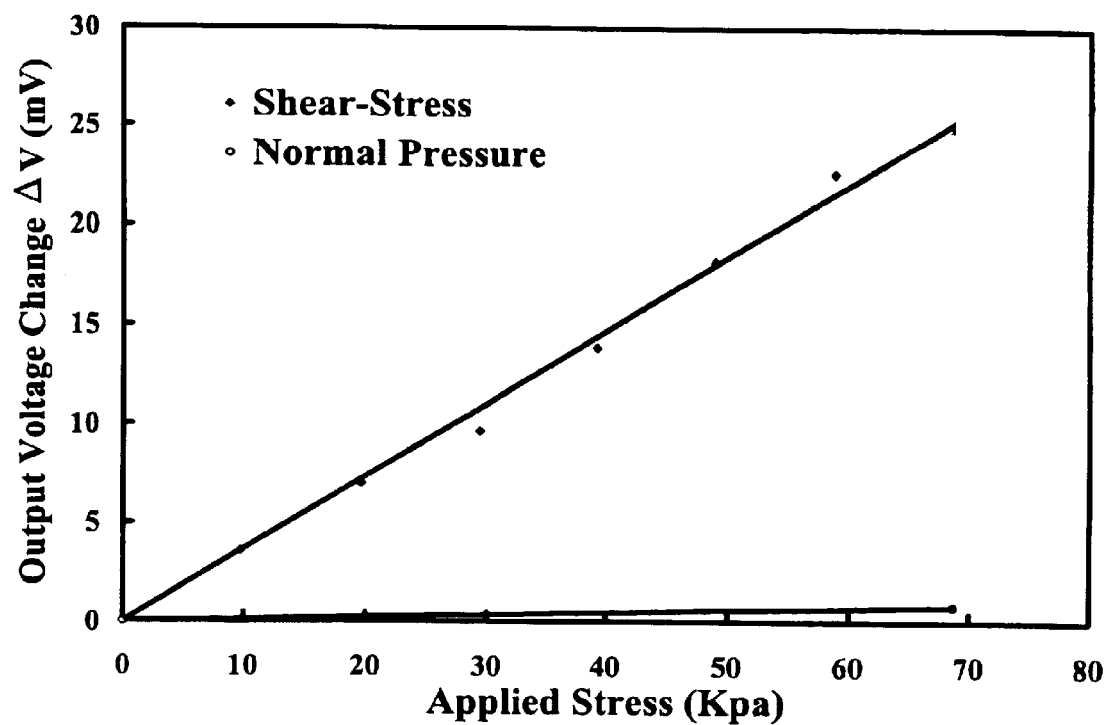

FIGS. 2(*a*)–(c) shows the 3-D structure of the sensor
FIG. 2(*a*) Top Front View;
FIG. 2(*b*) Section of the etched cavity of the Shear-Stress sensor;
FIG. 2(*c*) Back of the cavity.
FIGS. 3(*a*)–(h) indicates the steps of the preparation process.
FIG. 3(*a*) polish and implantation
FIG. 3(*b*) sputter to deposit $Si_3N_4$
FIG. 3(*c*) etching
FIG. 3(*d*) sputter to deposit $SiO_2$
FIG. 3(*e*) Connect the component
FIG. 3(*f*) Apply photo resistors
FIG. 3(*g*) from Flange.
FIG. 3(*h*) completed wiring of the unit
FIGS. 4(*a*)–(c) shows the SEM of the component preparation process
FIG. 4(*a*) Top Front View;
FIG. 4(*b*) Section of the etched cavity of the Shear-Stress sensor;
FIG. 4(*c*) Back of the cavity.
FIG. 5 shows the sensing and measuring systems of the sensor unit.
FIG. 6 shows that the unit has a pretty good Shear-Stress sensitivity, rarely affected by Normal Pressure.
●. . . Shear-Stress ○. . . Normal Pressure
FIGS. 7(*a*)–(c), the output response of the two X-shape parts near the $SiO_2$ Flange on the Shear-Stress sensing diaphragm depends on the Shear-Stress size and direction.
—●—x ducer 1 —O—x ducer 1
FIG. 7(*a*) x-coordinate direction Shear-Stress
FIG. 7(*b*) 45° direction Shear-Stress
FIG. 7(*c*) Y-coordinate direction Shear-Stress
FIG. 8 shows the Hysteresis of the Shear-Stress sensing component.
—●—forward —O—reverse

REFERENCE NUMBER OF THE ATTACHED DRAWINGS

1 . . . flange
2 . . . $SiO_2$
3 . . . diaphragm
4 . . . metal line
5 . . . X-shape piezoresistors
6 . . . Al electrode
7 . . . Glass Pyrex 7740
8 . . . . Au pad
9 . . . wire bonding
10 . . . ceramic substrate
11 . . . Si substrate
12 . . . photo resist
13 . . . implanted
14 . . . cavity
15 . . . $Si_3N_4$
30 . . . power supply
31 . . . constant current source
32 . . . RCLPF
33 . . . buffer amplification circuit
34 . . . A/D converter

DETAILED DESCRIPTION OF THE INVENTION

With a view to improving the defects of the above-mentioned sensing units and achieving the goal of high efficiency, a Contact-type micro piezoresistive Shear-Stress sensor is fabricated. That in accordance with the analytical results of FEM, taking the advantages of the Silicon Group Micro-Machining processing technology applied in MEMS, to measure the Shear-Stress produced between the socket and the stump skin. Therein X-shape piezoresistors as sensing units on the Contact-type micro piezoresistive Shear-Stress sensor. That have some difference between usual type, even though X-shape piezoresistors are similar to those reported by Jyh-Jier Ho et al on *International J. of Electronics*.

The Invention, the Contact-type Micro Piezoresistive Shear-Stress Sensor shown as FIG. 2. includes two X-shape piezoresistors, as the primary sensing units. These sensing units consist vertically of: (from bottom to top)

Si substrate (11): made of High Doping semi-conductor piezoresistive material;

Sensing diaphragm (3): formed into the etched cavities at preset locations on the Si substrate;

Protective Membrane: made of semi-conductor protective material like $SiO_2$, $Si_3N_4$, formed on the above-said membranes;

Flange (1): made of the same material as the above-mentioned Protective Membrane, and formed via etching technology at the preset positions on the said Membranes as Shear-Stress sensing components.

The X-shape piezoresistors of invention have specifically structure, a Flange (I) added right on the sensing diaphragm. Primarily, this structure is to help production of Shear-Stress on the sensing diaphragm (3) via rubbing and pulling of the stump skin, and the signals then will be transmitted through the X-shape piezoresistors implanted on the diaphragm (5) surface. The thickness of the sensing diaphragm is three times of the X-shape piezoresistive pressure sensor, which will reduces the influence of Normal Pressure and thus increases the measuring accuracy while the Contact-type Shear-Stress sensor is mounted on the surface of the stump.

Compared with traditional Shear-Stress sensors, the invention has the following features: first, use two X-shape piezoresistors as sensing components with a Flange on each sensing diaphragm. It is expected that the Shear-Stress produced on the sensing diaphragm can be enforced by rubbing and pulling of the stump skin, and then the signals received will be transmitted via the X-shape piezoresistors implanted on the diaphragm surface. Second, implant the X-shape piezoresistors between the middle of each side and the center of the diaphragm, letting less affected by Normal Pressure and more sensitive of Shear-Stress. Third, use Si group as the material for the invented Shear-Stress sensor, which is compatible with the current VLSI technology and can be applied to the development of ASIC (Application specific IC,), or mass produced in Array structures via VLSI's high technology to reduce the production cost.

Preparation Process: (please refer to the flow chart shown in FIG. 3.)

(a) Use N-shape silicon (100) polished on both sides, with 1~4 (obm-cm) resistance rating and 425±15 ($\mu$m) thickness, as the substrate (11); determine the two X-shape piezoresistors (5) positions and patterns by photo resistors (12) after cleaning; and implant Boron, with an energy of 14 Kev and a dosage of $2 \times 10^{15}$ ($cm^2$) by ion the implantation (13) method.

(b) Determine by the photo resistors the cavity areas to be etched; use a sputter to deposit $Si_3N_4$; and lift the $Si_3N_4$ away from the photo resistors.

(c) Etch $Si_3N_4$ in the KOH solution for 4.5 hours at a temperature of 70° C.; and then immerse in a solution of $HF:H_2O=1:10$ to remove $Si_3N_4$.

(d) Use a Sputter to deposit $SiO_2$ with a thickness of 3 $\mu$m at 400° C.

(e) Connect the component to a positive voltage and the glass Pyrex to a negative voltage in a Anode Bonding process, and then input a DC voltage of 1000V at 4000° C.

(f) Apply photo resistors to determine the positions and patterns of the Flanges.

(g) Etch $SiO_2$ in the BOE solution to obtain Flange.

(h) Etch $SiO_2$ in the BOE solution till openings through to the surface of the Si substrate to be the end positions of the two X-shape piezoresistors; and then do Shear-Stress tests after wiring of the unit is completed.

For preparation of the cavity structure of the sensor, it can be done by chemical etching solutions or physical etching techniques.

The Contact-type Micro Piezoresistive Shear-Stress Sensors invented by the Author et al have the following features:

(1) Use two X-shape piezoresistors as sensing units, and add a flange onto the sensing diaphragm, in order to help producing more Shear-Stress on the surface of the sensing diaphragm while the stump skin rubbing and/or pulling the surface of the prosthesis socket. The real values of the Shear-Stress measured will be analyzed and then signals transferred from the values will be transmitted via the X-shape piezoresistors implanted on the diaphragm surface.

(2) Implant the X-shape piezoresistors between the middle of each side and the center of the square diaphragm, having a smaller Normal Pressure influence and a larger Shear-Stress sensitivity.

(3) Since this kind of Shear-Stress sensor is made of materials of silicon group, it is compatible with VLSI technology and can be used in developing ASIC, or be mass produced in array structures via VLSI industrial technology to reduce its cost.

After experimenting the above-said features, the Invention is proved to have the following functions:

(1) The sensing unit presented in the Invention has a outstanding sensitivity of 3.6 uv/mA-Kpa to Shear-Stress, and hardly affected by Normal Pressure.

(2) The Shear-Stress sensor has a Hysteresis error lower than 8.9%FS—with an acceptable repeatability.

(3) The Invention has an almost linear relationship with temperature, and this feature indicates that the bias voltage of the Shear-Stress sensor is larger; with thicker diaphragms, transformation caused by the thermal stresses is less; where the X-shape piezoresistors of the Shear-Stress sensors are implanted are the positions of less effective stresses. Therefore, compared with the pressure sensor, the sensitivity of the temperature sensor is apparently lower.

SUCCESSFUL EXAMPLES

To illustrate the innovative, advanced and practical applications of the Invention and the features and contents of its preparation process, successful cases where the Contact-type Micro Piezoresistive Shear-Stress Sensors are applied are given below.

Figure 1:
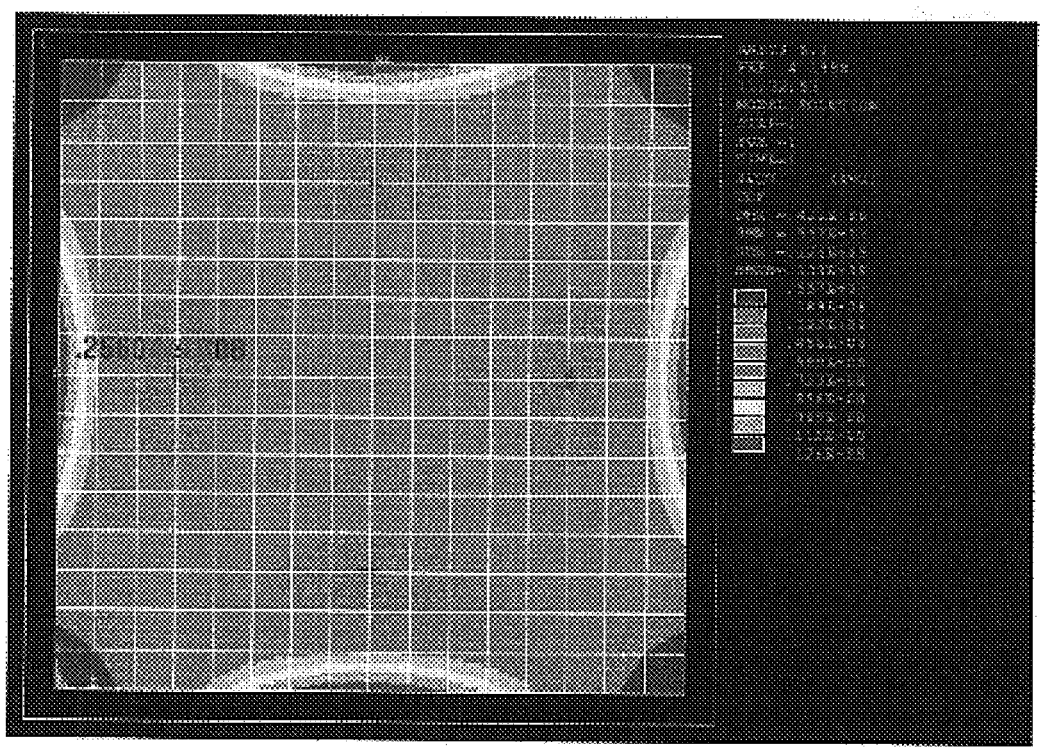
FIG. 1 shows the effective stress distribution while the diaphragm is loaded with 640 Kpa Normal Pressure, analyzed by FEM.

FIG. 1 shows the effective stress distribution while the diaphragm is loaded with 640 Kpa Normal Pressure, analyzed by FEM. The distribution from red to blue stands for the effective stress from maximum to minimum. As you can see, the maximum stress locates near the middle of each side of the square diaphragm, with its direction perpendicular to each edge. However, the minimum stress appears at the corners of the diaphragm. Therefore, the best position for setting the X-shape part of the Shear-Stress sensor should be near the middle of each side of the diaphragm.

FIG. 2 shows the 3-D structure of the sensor, and FIG. 3 indicates the steps of the preparation process. As shown in the Figuress, Si piezoresistive material (including Flange $SiO_2$), Glass Pyrex and Al electrodes are deposited respectively on the Single Crystal Si substrate. The size of the active area is 3,000×3,000 $um^2$, the thickness of the diaphragm is 300 um, and the size of the $SiO_2$ Flange is 1,100×1,100×3 $um^3$.

FIG. 4 shows the SEM of the component preparation process: (a) Top Front View; (b) Section of the etched cavity of the Shear-Stress sensor; (c) Back of the cavity.

FIG. 5 shows the sensing and measuring systems of the sensor unit. It consists primarily of a constant current source (31), a RC LPF (32), a buffer amplification circuit (33) and a A/D converter (34). Voltage needed for the Constant Current Source and 7410P Amp is supplied ± 12V by the Power Source (30), in order to keep the current at 5 mA that flows through one of the arms of the X-shape part. While measuring, apply a plane shear stress via PZT on the sensing Flange. Divide the obtained value by the contact area, and the Shear-Stress value of the active area can be figured out.

FIG. 6 shows that the unit 3.6 uv/mA-Kpa has a pretty good Shear-Stress sensitivity, rarely affected by Normal Pressure.

Figure 7A:
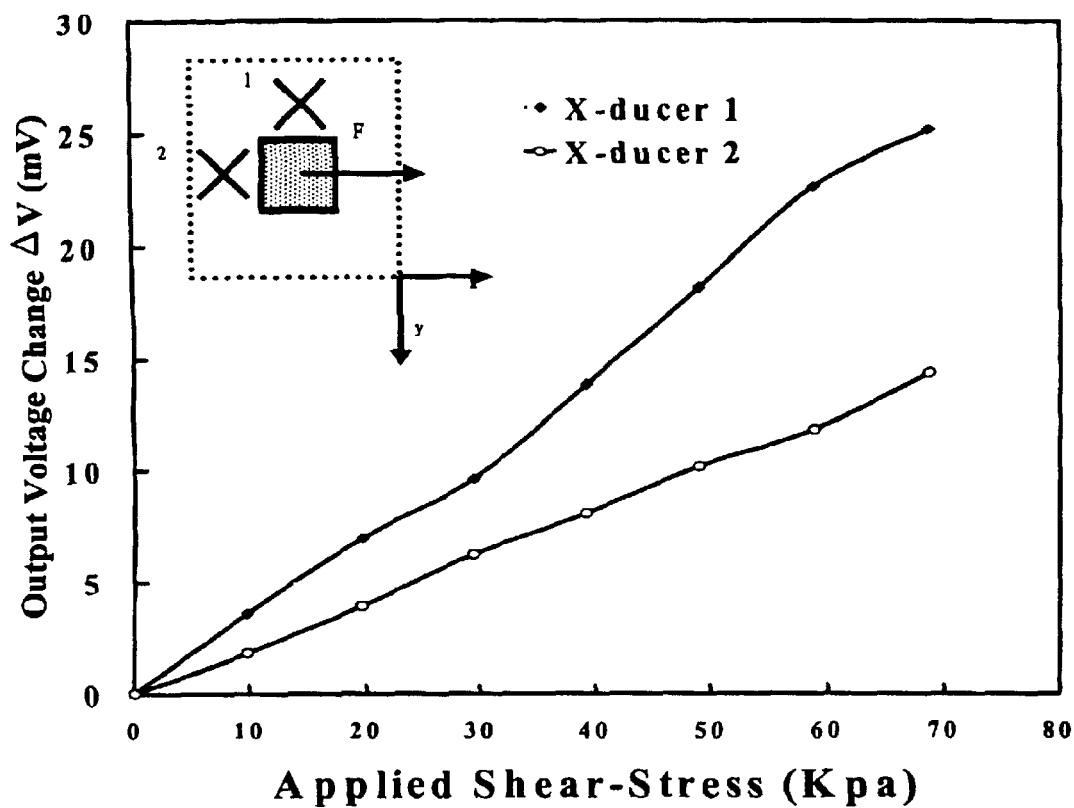
Figure 7B:
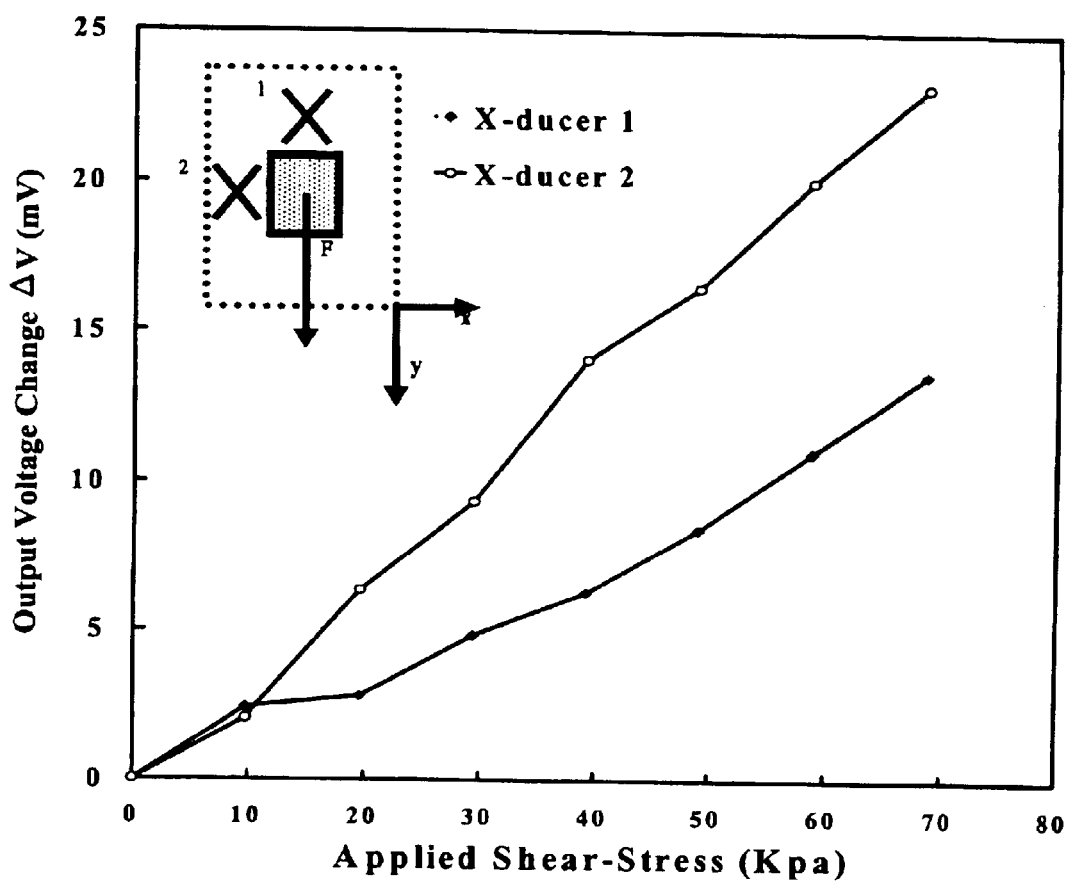
Figure 7C:
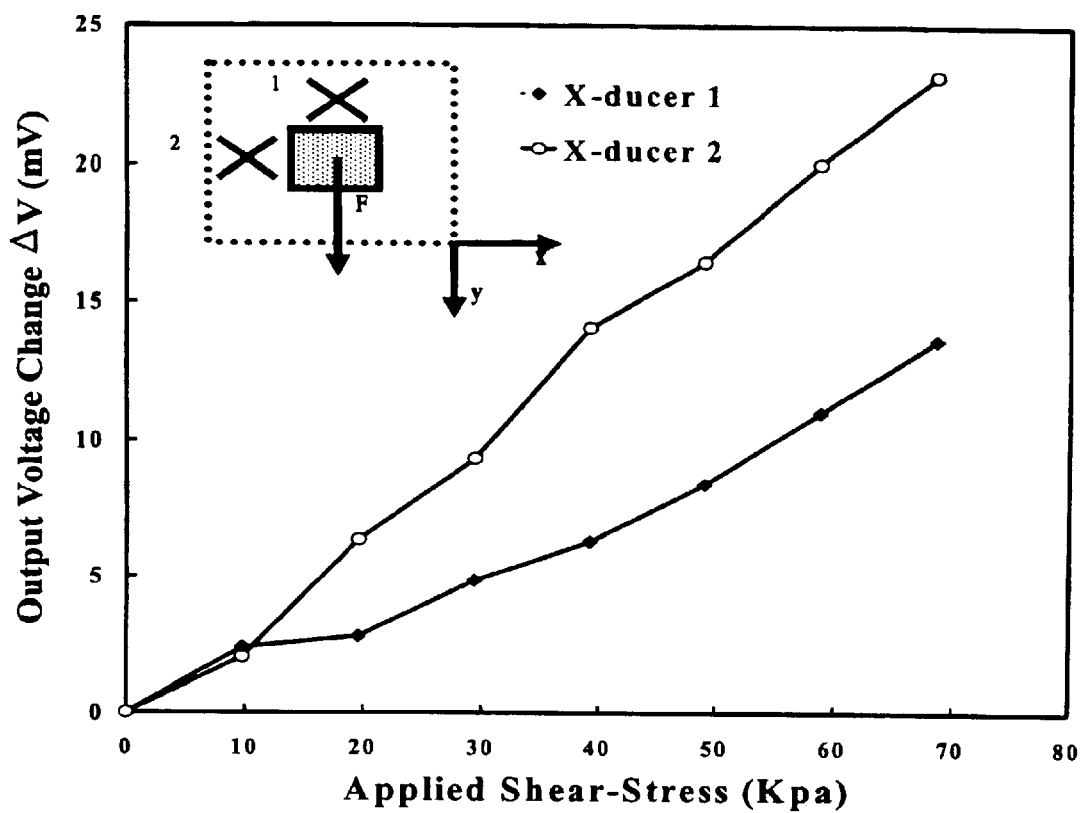
Figure 8:
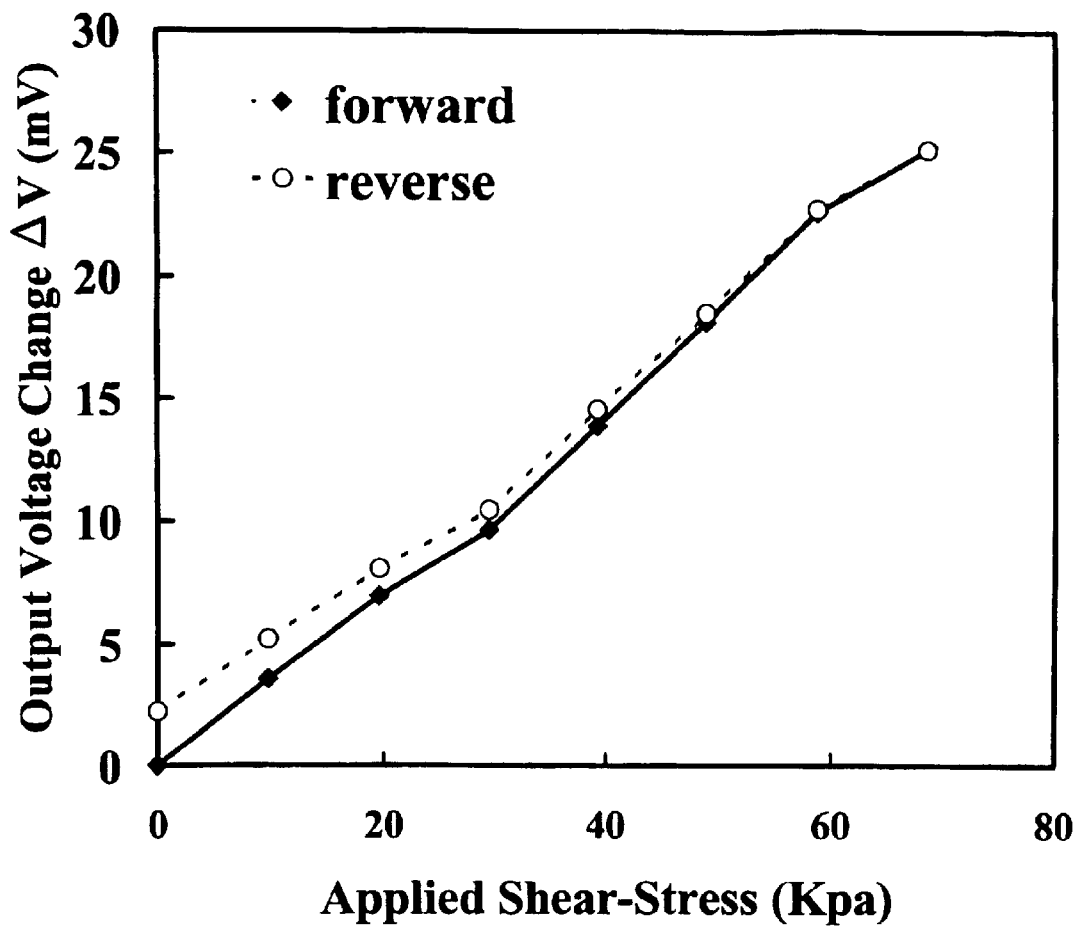

As shown in FIG. 7, the output response of the two X-shape parts near the $SiO_2$ Flange on the Shear-Stress sensing diaphragm depends on the Shear-Stress size and direction. From the output signals received by the two X-shape parts, not only the Shear-Stress size can be calculated, but also the direction of Shear-Stress on quarter of the diaphragm quadrant through the relationship between the relative positions of the two X-shapes and the relative size of the output signals. In this Figures, the Shear-Stress response sensitivity of one X-shape is two times of the other, meeting the preset design requirements.

FIG. 8 shows the Hysteresis of the Shear-Stress sensing component. As the Hysteresis error is lower than 8.9% FS, its repeatability is acceptable.

The Invention is a Contact-type Micro Piezoresistive Shear-Stress Sensor, having two X-shapes and a Flange as its main sensing unit.

What is claimed is:

1. A contact-type micro piezoresistive shear-stress sensor comprising:

a) a silicon substrate;

b) a sensing diaphragm formed into etched cavities at preset locations on the silicon substrate and having a substantially square shape;

c) a flange framed by means of etching technology at the center of said sensing diaphragm;

d) two X-shaped piezoresistors implanted at the center of adjacent longitudinal sides of said sensing diaphragm between the respective side and the center of said sensing diaphragm; and e) a protective membrane of semi-conductor protective material formed on said sensing diaphragm.

2. The contact-type micro piezoresistive sheer-stress sensor as defined in claim 1, wherein said flange is formed of the same material as said protective membrane.

3. The contact-type micro piezoresistive sheer-stress sensor as defined in claim 2, wherein said protective membrane and said flange are formed of $SiO_2$ or $Si_3N_4$.

4. The contact-type micro piezoresistive sheer-stress sensor as defined in claim 1, wherein said silicon substrate is formed of high doping semi-conductor piezoresistive material.

5. The contact-type micro piezoresistive sheer-stress sensor as defined in claim 3, wherein the formation of the flange comprises immersion in an etching agent at a concentration of $HF:H_2O$ of 1:10, and preparation of the semi-conductor is according to the process of pattern etching for size and shape.

* * * * *